United States Patent
Pohjanen et al.

(10) Patent No.: US 9,456,747 B2
(45) Date of Patent: Oct. 4, 2016

(54) GAZE GUIDANCE ARRANGEMENT

(71) Applicant: Trividi Oy, Oulu (FI)

(72) Inventors: Petri Pohjanen, Oulu (FI); Nora Kaarela, Helsinki (FI); Jukka Alasirnio, Jaali (FI)

(73) Assignee: Trividi Oy, Oulu (FI)

( * ) Notice: Subject to any disclaimer, the term of this patent is extended or adjusted under 35 U.S.C. 154(b) by 0 days.

(21) Appl. No.: 14/424,305

(22) PCT Filed: Sep. 12, 2013

(86) PCT No.: PCT/FI2013/050881
§ 371 (c)(1),
(2) Date: Feb. 26, 2015

(87) PCT Pub. No.: WO2014/041248
PCT Pub. Date: Mar. 20, 2014

(65) Prior Publication Data
US 2015/0208919 A1    Jul. 30, 2015

(30) Foreign Application Priority Data

Sep. 12, 2012  (FI) .................................... 20125945
Jan. 16, 2013  (FI) .................................... 20135047

(51) Int. Cl.
| | |
|---|---|
| A61B 3/14 | (2006.01) |
| A61B 3/113 | (2006.01) |
| A61B 3/12 | (2006.01) |
| A61B 3/00 | (2006.01) |

(52) U.S. Cl.
CPC .............. *A61B 3/14* (2013.01); *A61B 3/0008* (2013.01); *A61B 3/0025* (2013.01); *A61B 3/0091* (2013.01); *A61B 3/113* (2013.01); *A61B 3/12* (2013.01)

(58) Field of Classification Search
CPC  A61B 3/0025; A61B 3/0083; A61B 3/0091; A61B 3/032; A61B 3/10; A61B 3/113; A61B 3/12; A61B 3/132; A61B 3/14
USPC .................... 351/204, 205, 208–211, 206
See application file for complete search history.

(56) References Cited

U.S. PATENT DOCUMENTS

| | | | | |
|---|---|---|---|---|
| 5,070,883 A | * | 12/1991 | Kasahara | ................ F41G 3/225 351/209 |
| 5,920,375 A | * | 7/1999 | Fahle | ..................... A61B 3/024 351/224 |

(Continued)

FOREIGN PATENT DOCUMENTS

WO    2007085682 A1    8/2007

OTHER PUBLICATIONS

International Search Report for FI20135047 dated Sep. 16, 2013.
(Continued)

*Primary Examiner* — Huy K Mai
(74) *Attorney, Agent, or Firm* — Andrus Intellectual Property Law, LLP

(57) ABSTRACT

A gaze guidance arrangement is formed in a device for imaging an eye, the device being wearable on the object to be examined or otherwise placeable to the front of an eye or eyes. The device comprises one or more camera arrangements and an illumination arrangement. The gaze guidance arrangement comprises a visual target, to which the gaze is supposed to be directed, in order to reach the desired position of the eye, and a control arrangement that guides the gaze guidance arrangement. The control arrangement is at least partly located in said device and further guides the imaging process of the device and the device takes images automatically when the eye is in a predetermined position to which the visual target has directed said eye. The gaze guidance arrangement comprises one or more target formation arrangements that is provided to form a visual target, the location of which in respect of the eye or the viewing direction of the eye or to both can be changed, and the location of the visual target is determined such that as the eye is directed to it or in its direction, it is in said predetermined position.

21 Claims, 4 Drawing Sheets

(56) References Cited

U.S. PATENT DOCUMENTS

| | | |
|---|---|---|
| 2004/0263784 A1 | 12/2004 | Cornsweet et al. |
| 2006/0114412 A1 | 6/2006 | Tawada |
| 2009/0096986 A1 | 4/2009 | Teige et al. |
| 2011/0170060 A1* | 7/2011 | Gordon .................. A61B 3/113 351/206 |
| 2012/0133889 A1 | 5/2012 | Bergt et al. |

OTHER PUBLICATIONS

International Search Report and Written Opinion for PCT/FI2013/050881 dated Dec. 10, 2013.

International Preliminary Report on Patentability for PCT/FI2013/050881 dated Jun. 30, 2014.

\* cited by examiner

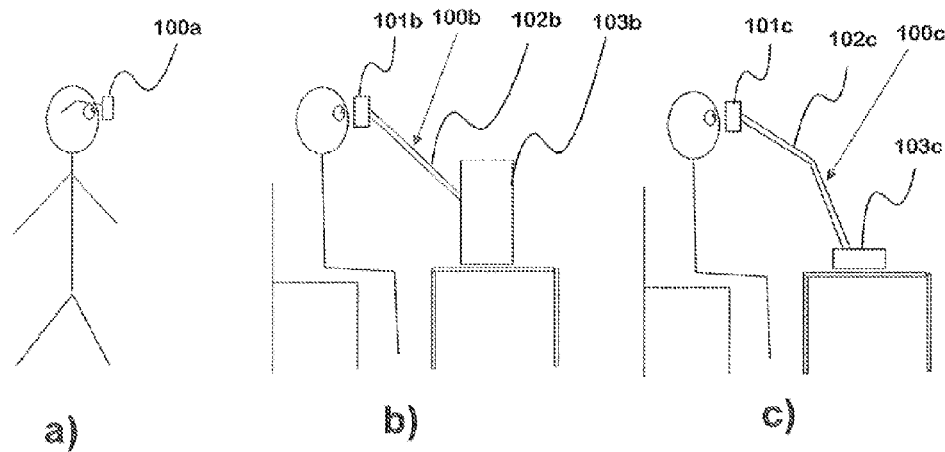
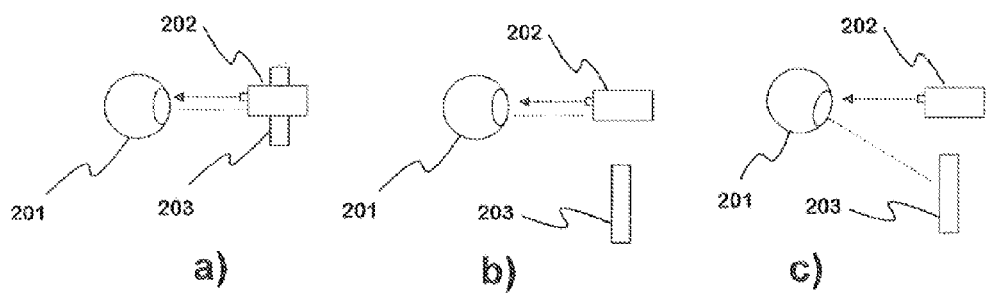
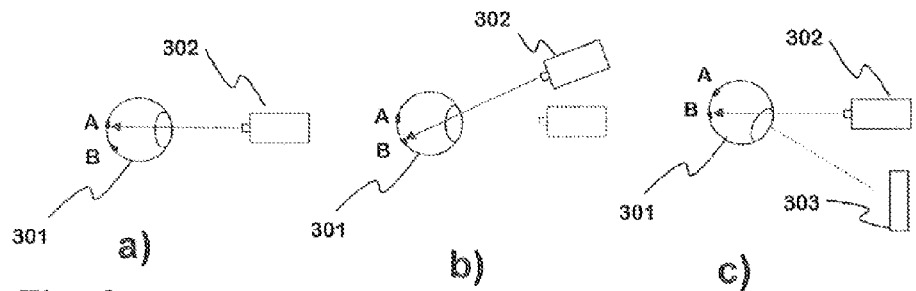
Fig. 1
Fig. 2
Fig. 3

GAZE GUIDANCE ARRANGEMENT

CROSS-REFERENCE TO RELATED APPLICATIONS

This application is the U.S. national stage application of International Application PCT/FI2013/050881, filed Sep. 12, 2013, which international application was published on Mar. 20, 2014, as International Publication WO2014/041248 in the English language. The international application is incorporated herein by reference, in entirety. The international application claims priority to Finnish Patent Application No. 20125945, filed Sep. 12, 2012, and Finnish Patent Application No. 20135047, filed on Jan. 16, 2013, which are incorporated herein by reference, in entirety.

The invention relates to a gaze guidance arrangement, provided to guide the movement or position of an eye or both, comprising a visual target, to which the eye is supposed to be directed.

PRIOR ART

Eyes and especially fundi are imaged in order to detect different diseases or their symptoms. For example, in diabetes, damages may arise in fundi, which damages should be discovered as soon as possible. Devices used for this are called oftalmoscopes or fundus cameras of an eye, and in those the inner parts of an eye are examined by illuminating it through the pupil. Usually, when using a fundus camera, the person to be examined places her/his head into the examining device, and one or more trained person(s), such as a doctor, adjusts and moves manually the examining device and observes the object and, when necessary, launches manually the imaging device to take an image. Both eyes of the person to be examined are examined separately. This is a slow procedure and requires work contribution of a trained person.

Because the pupil of the eye contracts when light is directed thereto, the examinations are usually performed in a darkened room, and furthermore, eye drops can be used that enlarge the pupil and prevent it from contracting. Some patients, for example children, don't necessarily like applying of eye drops and recovering from the effect of them takes a long time. The patient and the nursing staff have to wait until the drops start to take effect before the examination can be performed. This stows down considerably the performing of the examination and also increases the threshold of the patient to go, for example, to routine examinations.

One problem in imaging an eye and fundi is the wrong position of the eye in respect of the imaging device. Thereby, it is necessary to wait that the object moves her/his eye to the right position, or the user of the device has to actively guide the object to look at a certain direction. This has been realized, for example, so that the user of the device instructs the object to look at, for example, some point in a board on the wall or asks the object to look at the hand that the user is moving. This requires experience from the user and slows down the imaging.

In automatized eye imaging one problem is that the devices become quite large and clumsy, when automatic focusing and similar properties are tried to be accommodated in the device. It would be a remarkable advantage if the size of the apparatus could be reduced such that even the person to be examined herself/himself could place the device in position and start the imaging, in practice, with the present technique even an automatized device requires at least a trained assistant to use it.

SUMMARY

The object of the invention is a solution, by which the disadvantages and draw-backs of the prior art can be diminished. Particularly, the object of the invention is a solution, by means of which a gaze guidance arrangement to an automatically operating device for imaging an eye is provided that would speed up the operation of the device and improve the reliability of the imaging result for diagnosis or monitoring without active operation of the device.

The objects according to the invention are achieved by a gaze guidance arrangement, characterized in what is disclosed in the independent claim. Some preferred embodiments of the invention are disclosed in the dependent claims.

The main idea of the invention is to form a gaze guidance arrangement for a device for imaging an eye that can be worn on the object to be examined or otherwise placed to the front of an eye or eyes. The gaze guidance arrangement comprises a visual target, to which the gaze is supposed to be directed, in order to reach the desired position of the eye, and a control arrangement that guides the gaze guidance arrangement. The control arrangement is at least partly located in said device and further guides the imaging process of the device, and the device takes images automatically when the eye is in a predetermined position to which the visual target has directed said eye. The predetermined position does not have to be the direct direction of view to the visual target, but the position in question can be reached before the eye is directed to the visual target. Thus, it may be sufficient that the desired position of the eye is reached when the direction of view moves towards the visual target.

According to an embodiment of the invention the gaze guidance arrangement is provided to guide the movement or position of an eye or both, the gaze guidance arrangement comprising a visual target, to which the eye is supposed to be directed. In a preferred embodiment of the invention, said gaze guidance arrangement comprises a control arrangement that is provided to guide the gaze guidance arrangement, the control arrangement being located at least partly in the device that is provided for examining an eye or eyes to be placed on the head of the object or to the front of the head of the object. The device comprises one or more camera arrangements and one or more illumination arrangements, the optical axes of the camera arrangement and the illumination arrangement used in the same imaging are in different directions or substantially apart from each other in relation to the eye, and said control arrangement is further provided to guide said camera arrangement and illumination arrangement. The control arrangement is provided to switch the camera arrangement to take automatically one or more images of the eye, when the eye is in a predetermined position, to which the visual target of said gaze guidance arrangement has guided said eye when the device is ready for operation in front of the eye, and one or more target formation arrangements that is provided to form said visual target the location of which in respect of the eye or the direction of view of the eye or to both can be changed, and the location of the visual target is determined such that as the eye is directed to it or in its direction, it is preferably in said predetermined position.

In an embodiment of the gaze guidance arrangement according to the invention, the gaze guidance arrangement comprises an arrangement for recognizing the position of the eye, and the control arrangement is provided to switch the camera arrangement to take automatically one or more images of the eye, when the arrangement for recognizing the position of the eye has recognized that the eye is in a predetermined position, to which the eye was guided by the visual target of said gaze guidance arrangement.

In a second embodiment of the gaze guidance arrangement according to the invention, in the gaze guidance arrangement the control arrangement is provided to guide the location of the visual target formed by the target forming arrangement according to the recognized position of the eye.

In a third embodiment of the gaze guidance arrangement according to the invention, said device comprises a sensor arrangement for detecting the movement or the position of the device or both, and said sensor arrangement is provided to transmit the detected information to the control arrangement that is provided, according to predetermined instructions, to change the operation of the gaze guidance arrangement by changing the location of the visual target according to the information of said sensor arrangement.

In a fourth embodiment of the gaze guidance arrangement according to the invention, the gaze guidance arrangement is located partly outside of said device, and the device is provided so that when the device is in its place and ready for operation, the direction of viewing of the eye to be guided is through the device or passing by the device, and the part outside of the device is at least a part of the target forming arrangement.

In a fifth embodiment of the gaze guidance arrangement according to the invention, the target forming arrangement outside of the device is a display or similar device on which it is possible to form said visual target, or a surface or similar, on which said visual target can be reflected by a light source arrangement capable of being controlled.

In a sixth embodiment of the gaze guidance arrangement according to the invention, in said device or in connection with it there is a recognizing arrangement that is provided to recognize the location of the visual target, the location being provided to be transmitted to the control arrangement.

In a seventh embodiment of the gaze guidance arrangement according to the invention, the visual target is at least during the guidance of the eye immobile in order to achieve at least one predetermined position of the eye, and in operation mode the immobile device is arranged to be movable.

In an eighth embodiment of the gaze guidance arrangement according to the invention, the visual target is provided to be movable according to the movements of the device such that the location of the visual target in respect of the direction of the viewing of the eye remains substantially the same.

In a ninth embodiment of the gaze guidance arrangement according to the invention, at least one target forming arrangement is located in said device.

In a tenth embodiment of the gaze guidance arrangement according to the invention, the target forming arrangement or at feast part of the components thereof in the device are separate for both eyes, respectively, or the target forming arrangement or at least part of its components are common for both eyes, and the device comprises an arrangement for moving said common components or the target forming arrangement inside the device to the vicinity of the eye the position of which is to be guided by the gaze guidance arrangement.

In an eleventh embodiment of the gaze guidance arrangement according to the invention, the target forming arrangement in the device comprises an internal light source arrangement that is provided to form a visual target, the light source arrangement comprising one or more light sources.

In a twelfth embodiment of the gaze guidance arrangement according to the invention, the internal light source arrangement is provided to form a visual target by illuminating towards the eye, in a thirteenth embodiment of the gaze guidance arrangement according to the invention, the internal light source arrangement consists at least partly of the illumination arrangements of the device. In a fourteenth embodiment of the gaze guidance arrangement according to the invention, the internal light source arrangement is provided to form a visual target by illuminating the surface inside the device or a similar structure.

In a fifteenth embodiment of the gaze guidance arrangement according to the invention, when the device is standing still in operation mode, between the internal light source arrangement of the device and the eye guided by the gaze guidance arrangement there is an optics arrangement that may consist of one or more optical components, such as lens, mirror, prism or similar, the optics arrangement being provided to form an image of the visual target at different distances in respect of the eye.

In a sixteenth embodiment of the gaze guidance arrangement according to the invention, at least one infernal light source arrangement of the device consists of one or more light sources that are provided to be switched on and off according to the instructions of the control arrangement, in order to form a visual target. The brightness of the light source can also be adjusted, i.e. it can be dimmed or brightened. In a seventeenth embodiment of the gaze guidance arrangement according to the invention, at least one internal light source arrangement of the device consists of one or more light sources that are movable inside the device or the direction of illumination of which can be changed, or both, in respect of the eye guided by the gaze guidance arrangement.

In an eighteenth embodiment of the gaze guidance arrangement according to the invention, said device comprises an image analysing arrangement or a connection to an image analyzing arrangement, the image analysing arrangement being provided to recognize predetermined features or properties in an image taken by the camera arrangement or in the image area of the camera arrangement and to transmit the information to the control arrangement being provided according to predetermined instructions stored in the control arrangement and information of the image analysing arrangement to form a visual target, if the predetermined instructions become filled. In a nineteenth embodiment of the gaze guidance arrangement according to the invention, the predetermined instructions stored in the control arrangement include at least one of the following: a reflection detected in the image or image area, success of imaging of a certain image area, failure of imaging of a certain image area, eye position or getting the eye to be in a certain position in respect on the camera arrangement.

In a twentieth embodiment of the gaze guidance arrangement according to the invention the visual target is point-like or a pattern or a point deviant of its environment by its colour, the visual target being immobile or movable in order to provide the desired position or movement of an eye in respect of the camera arrangement.

An advantage of the invention is that with it the operation of the device imaging an eye and a fundus can be improved automatically by guiding the eye to a preferred position in respect of the imaging. Thereby, moving of the cameras or imaging optics of the device is avoided or can be reduced.

An advantage of the invention is that by means of it an eye can be examined at a point that would otherwise not necessarily be possible or would require more expensive and complicated equipment. By means of it, for example, moving mechanisms of camera arrangements can be replaced by mechanisms with a smaller trajectory. Likewise, camera angles or measurement points can be achieved which are otherwise difficult or unattainable.

A further advantage of the invention is that by means of it the eye can be brought into the same position as in a previously performed examination, whereby the results are more comparable.

A device designed for examining of an eye, with a gaze guidance arrangement according to the invention, can be adapted to examine properties of an eye that the device would not otherwise examine, such as speed, extent, limits of movements or saccadic movements of an eye.

When imaging, for example, the fundus of an eye, different layers and optical structures of the eye cause reflections. An advantage of the invention is that by means of it these reflections can be minimized or avoided completely. Further, if the camera arrangement and the individual parts in it are moved possibly by means of separate guiding motors, the movement of it or them can be combined in a dynamic gaze guidance system and thus an optimal imaging point can be reached as soon as possible. This is emphasized particularly when imaging is performed with a greater accuracy either by optics designed for this or by a digital or an optical zoom.

Further, an advantage of the invention is that it is applicable to different types of eye imaging. The person to be imaged can also sit, stand or lay on a bed. Further, the invention reduces the time spent in a routine examination. Likewise, it reduces the need of trained personnel in such examinations.

An advantage of the invention is further that it enables automatic searching and quick checking of the detected deviations. By deviation a detectable and followable change is meant caused by a disease or similar.

DESCRIPTION OF THE FIGURES

In the following, the invention will be described in detail. In the description, reference is made to the enclosed drawings, in which FIG. 1 shows examples of a device where a gaze guidance arrangement according to the invention is used, FIG. 2 shows an example of the operation of a gaze guidance arrangement according to the invention, FIG. 3 shows another example of the operation of a gaze guidance arrangement according to the invention.

DETAILED DESCRIPTION OF FIGURES

Figure 4:
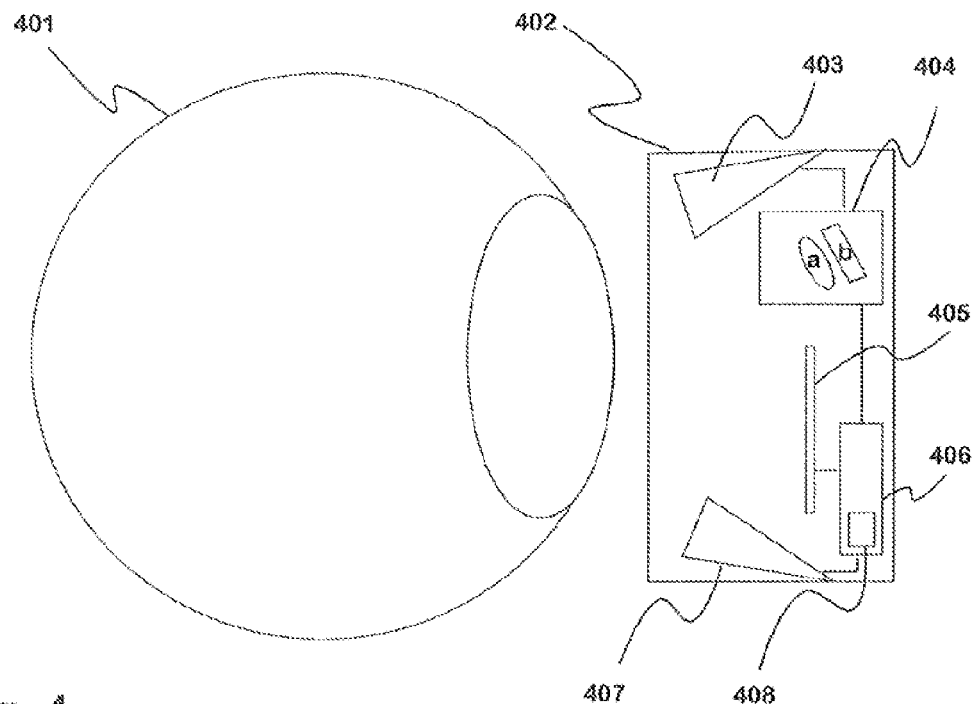
FIG. 4 shows an example of a gaze guidance arrangement according to the invention located in a device.

The embodiments in the following description are disclosed as examples only, and someone skilled in the art may realize the basic idea of the invention also in some other way than what is described in the description. Though the description may refer to a certain embodiment or embodiments in several places, this does not mean that the reference would be directed towards only one described embodiment or that the described characteristic would be usable only in one described embodiment. The individual characteristics of two or more embodiments may be combined and new embodiments of the invention may thus be provided.

FIG. 1 shows three examples of the device 100, where the gaze guidance arrangement according to the invention is used. Let us remind in this connection that the images are simplified, in order to make the essential principle of the invention clearer. The device according to the invention can be realized by very many different formations.

Device 100 is meant to image the eyes of the object. The device comprises one or more camera arrangements. The camera arrangements are placed in the device such that when the device is placed to the front of the eyes of the object, the camera arrangement is substantially at the location of the eye. There may be several camera arrangements per eye. The camera arrangements can be fixed, i.e. they have one imaging direction, or they are movable by the motor arrangement. With two camera arrangements the imaging can be performed for both eyes at the same time or nearly at the same time. The imaging can of course be performed in turn for each eye.

The device can be wearable on the object to be imaged, that is, it can be like the example of FIG. 1a, where the device 100a resembles eyeglasses, the frames of which are supported on the sides of the head. The frames can also extend behind the ears, or they can be short for the directing. A device to be worn on the object can be realized also in many other ways. It can, for example, resemble a cap or a helmet, and the imaging part of the device is in a visor that is lowered to the front of the eyes and positioned to the imaging position. The device 100b can be realized such that it comprises a part 101b which comprises at least camera arrangements and illumination arrangements, which part is placed to the front of the eyes correspondingly to the embodiment to be worn on the object. The part of the device to be placed to the front of the eyes is fixed to a movable structure 102b which can be moved to different imaging positions depending on the object to be examined. Other functional parts of the device can be placed in a part 103b that will not be worn on the object. Such an embodiment is shown in the example of FIG. 1b. Said other functional parts can, of course, be located in the part placed to the front of the eyes. Such an embodiment is shown in the example of FIG. 1c. The part 101c of the device 100c to be placed to the front of the eyes is similar to device 100a as to its functionalities, but it is fixed onto a movable structure 102c in the support part 103c that in this example operates mainly as a counterweight.

The device can be realized also binocular-like, whereby the object of the imaging holds the device in front of her/his eyes. The part placed to the front of the eyes can be arranged to be movable such that the place or position can be altered, when it is at its position for the imaging event. This can also be arranged to be performed such that the person to be imaged adjusts the position of the device. This can also be done by the supervisor of the imaging, for example, if the object of the imaging is a child or otherwise not able to adjust the position. The position can be selected and adjusted also automatically. Thereby, for example, the motor arrangement of the device guides the support to be placed on the nose and thus places the device into the position where the imaging is performed. The device can also comprise other features by which the desired position is achieved and the device is made to stay there during the imaging. Such may include, for example, different stickers, suction pads, vacuum pumps or similar.

The device according to the examples of FIG. 1 comprises a support structure which surrounds the eye or eyes completely or partly. By means of the support structure, the device can be supported when it is in its place, and by means of it the device can be positioned to the measuring position or close to it such that the device's own adjustment can be reduced. By means of the support structure the device can also be hold in its place during the measuring. The support structure is placed against skin. The support structure is made preferably completely or partly of resilient material in order to make its placing and wearing against skin more comfortable for the object.

The support structure can also be arranged to cover both eyes such that no diffused light gets to the eyes or the amount of it can be adjusted. Then, the device is at least partly against the skin of the object. The support structure is either completely or partly impermeable to light. Thereby, the eye is in a darker environment and the pupil of the eye can be made as large as possible prior to taking the image. For example, a transparent area can be left in the support structure for an external gaze guidance of the device. This transparent area can be realized, for example, so that on top thereof there is a cover that can be opened and closed such that it is useable only when necessary. The support structure, and similarly other parts of the device in front of the eyes, can be made such that, when necessary, it can be dimmed in a desired way at different places in order to reduce the diffused light in connection with the imaging. This can, for example, be realized such that the support structure consists of two overlapping surfaces in different polarisations.

The device can naturally be realized also in a way that there is no actual support structure, but the device performs the imaging in front of the eye.

The device comprises one or more illumination arrangements that can preferably be controlled. This may be in connection with the camera arrangement or separately, if the illumination arrangement is in connection with the camera arrangement, it can be arranged to be movable in the same time with the camera arrangement such that the illumination fakes place in an advantageous direction from point of view of the imaging. The illumination arrangement can also be fixed, i.e. it is directed into a certain direction. The device may also comprise more illumination arrangements that are directed in different directions, and those can be used alternately. The illumination arrangements can operate, for example, in visible light and infrared light areas. The different illumination arrangements of the device can operate in different wavelength regions. The illumination arrangements can be realized, for example, by LED lighting fixtures, halogen technique, laser, bulbs or in some other way. The illumination arrangements can operate by being switched on for a predetermined time or by producing a flashlight type flash. If the illumination arrangement can be directed, it is moved by the motor arrangement. The illumination arrangement can include optics which can be adjustable, for example, for positioning of the light, illumination arrangements of different types can be directed to different functions. The illumination arrangements are situated in respect of the camera arrangements in a way that they are separated from each other so that their optical axes do not meet.

Substantially, in the imaging of the eye, the camera arrangement and the illumination arrangement are situated in respect of the eye in a way that the optical axes of the camera arrangement and the illumination arrangement in respect of the eye are of different directions or substantially apart from each other. Thereby, the imaging of the eye and the illumination are performed from different directions or at least from different locations. These directions or locations are preferably adjustable, i.e. the location or direction or both of the camera arrangement or the illumination arrangement or both can be changed. Thereby the directions of the imaging and illumination change. Changing the directions of the imaging and illumination may lead to a situation where their optical axes in respect of the eye would be in the same direction. Thereby, said optical axes are, however, substantially apart from each other. In addition to the change of directions of the imaging and illumination, also changing of the position of the eye in respect of the imaging and illumination can be used. Then, a gaze guidance arrangement is used which will be described later. When the illumination and imaging are in different directions, i.e. the directions of the camera arrangement and the illumination arrangement in respect of the eye are different, no beam splitters are required in the device, and also the amount of other components can be reduced. Since also the illumination arrangement and imaging arrangement can be situated closer to the surface of the eye than in prior art, the device can be formed smaller than the devices of the prior art. Since the directions of the illumination arrangement and the camera arrangement in respect of the eye, and, when necessary, also the position of the eye can be changed, the imaging event can be optimised by means of the control arrangement and image analysing arrangement (will be described later), in this optimisation the positions of the illumination arrangement and the camera arrangement in respect of the surface of the eye are changed and the combination of positions is selected that is best suitable for the imaging event.

When the illumination and the imaging are in different directions, the illumination arrangement and the camera arrangement do not go in the way of each other, that is, they are at such distances from the surface of the eye and situated to each other in a way that they do not cover each other. Because the positions of the illumination arrangement and the camera arrangement in respect of the surface of the eye can be changed, an embodiment can be realized where the direction of light is random, and during the imaging the direction of light is selected that is the best for the imaging in question. Thus, the light is directed to the fundus of eye from a random spot in relation of the camera arrangement, in order to be able to perform the imaging as quickly as possible and without any special arrangements used in prior art for aligning the head, eye, pupil and fundus in respect of the imaging light of the fundus of eye on the same axis and in respect of the light coming onto the camera arrangement. In the invention, minimizing of the imaging arrangements results, however, in harmful reflections coming from the surface of the eye.

When the imaging and the illumination are divergent, a situation will become obvious whereby the light of the illumination arrangement is reflected from the surface of the eye to the camera arrangement. Since this reflecting light is substantially brighter than the data aspired after in the imaging, the reflecting light, i.e. reflection impedes the imaging and, in the worst case, ruins the whole imaging. This is difficult to evaluate in advance with different persons to be imaged, since the amount and character of the reflections depend partly on the humidity of the eye and the shape and position of the eyeball. In the invention, this problem is excluded in a way described later.

It is also possible that by changing the directions of the illumination arrangement or camera arrangement or both a desired image can not be provided or an error state can not be corrected. Thereby, the situation can be corrected by guiding the eye to another position. This can be done by the gaze guidance arrangement according to the invention.

The device according to the example of FIG. 1 comprises a power supply for operating the different parts of the device. This may be an accumulator or a battery or a connection to an external power supply, or similar. The device can also be provided to be charged by placing it in a dock charger or to charge it by wireless means. This is not shown in the figures. The device further comprises an arrangement by which is switched on. This may be, for example, a switch, the switching of which causes initialization of the functions of the device and moving to the operation mode. The device may also comprise some other arrangement, by which it is moved to the operation mode. In the operation mode, the device can check whether it is in its position in the front of the eyes. This may have been realized, for example, by different detectors. The part of the device to be placed in the front of the eyes may comprise an electronic or mechanical detector to detect whether it is pressed against the skin. This can also be realized by identifying reflection properties of an eye or eyes. In defecting the distance, also an image analysing programme can be used, where, for example, the size of the eye is recognized, or the camera arrangement is focused as a default for a predetermined distance, and when the image is sharp, the imaging area of the camera arrangement or the operating area of its own focusing motor is reached. The device can also be started manually to perform the imaging when it is placed in its position. This can be done by the supervisor or object of the imaging when he/she feels that the device is placed in its position. The device is provided also for switching itself off or for shifting to a standby mode when the imaging was performed acceptably. The device can further be realized such that it is placed in a dock charger or similar arrangement and it starts when it is removed from the dock charger and switches off when it is returned to the dock charger.

The device may comprise a motor arrangement that consists of one motor or more, it is provided to move the movable parts of the device which can include camera arrangements, different optics, illumination arrangements, different covers, such as, for example, the part of the device, through which the eyes of the object are being imaged, that can be covered when the device is switched off or in standby mode, in order to prevent dirt or excessive light from going into the device, which can impair the camera sensors of the camera arrangements.

The device comprises a control arrangement for controlling the parts and functioning of the device. This may have been realized by means of a memory or one or more processors, and the operating procedures are stored in the memory and are performed in a processor in order to give operating commands to different parts of the device. The control arrangement may also be an embedded system. The control arrangement is provided for transmitting and receiving data. The control arrangement can, for example, transmit the images taken by it forward, and it can receive imaging instructions or other data related to its operation. The device also comprises an image analysing arrangement or a connection thereto, which arrangement analyses the images taken by the device, or directly data coming from a camera sensor. The image analysing arrangement is provided such that it operates in real time or almost in real time, i.e. it performs an analysis for an image taken by the camera arrangement of the device as soon as the image was taken, and preferably before the next image will be taken. The image analysing arrangement comprises an arrangement to contact the control arrangement.

The control arrangement controls the operation of the camera arrangements and illumination arrangements, i.e. the fact when and where images are being taken from and how the illumination operates. The control arrangement can have an instruction for imaging stored in its memory which instruction can, for example, guide to image a part of retina or other part of the eye that one is interested in. The control arrangement guides the camera arrangement to take one image or a series of images from the desired point, which images are combined in an entirety in the device or, for example, in an external server. The control arrangement can also instruct the imaging to be performed when it is possible without actual searching of the object. The parameters of the images, i.e., for example, from which point the image will be taken, at which distance, with what kind of illumination, with which camera arrangement, with which duration of illumination and similar, can be changed for example by changing the operation and positions of the camera arrangements and illumination arrangements or by changing the position of the eye by means of a gaze guidance arrangement, or by combinations thereof. The control arrangement also controls other measurements or measures to be performed with the device.

The control arrangement can receive external commands, for example, in order to perform the imaging at the same time as it performs its stored commands. For example, part of the operation of the cameras can be controlled from outside of the device, and part of the operation of the cameras from the device. The device can also comprise an arrangement with which instructions are given to the object to be examined. These can include, for example, voice messages or light signals or instructions on an internal display. This arrangement is also controlled by the control arrangement.

The control arrangement guides the image to be checked by the image analysing arrangement. For example, the image analysing arrangement checks whether there are reflections in the image taken or in the image area, i.e. whether there is light of the illumination arrangement reflected from the surface of the eye. Thereby, no data can be obtained from the image, and the image is useless either completely or partly. The image analysing arrangement can perform this checking, for example, by means of the pattern recognition automatism when the reflections are clearly recognizable shapes in the image, or for example by studying the values of the pixels of the image or the values of the real-time image information obtained from: the camera and by detecting the reflection included in the image, if the values of a pixel group exceed a given limit value. These can be done also directly from the camera sensor without actual imaging. The reflections are nearly always brighter than the aspired image data. When the image analysing arrangement detects a reflection, it transmit the data to the control arrangement.

The image analysing arrangement can be adapted to recognize the position of the eye, whereby it operates as an arrangement for recognizing the position of the eye. This can be done, for example, by recognizing the location of the pupil in respect of the device or parts of the device or other known reference point. A reference image can also be taken of the eye, when it is in a known position, and the image obtained by the image analysing arrangement can be compared with this reference image and thus the position of the eye can be calculated.

An arrangement for recognizing the position of the eye can also be realized in other ways. The device can, for example, comprise a device, based on distance measuring, measuring the shapes of surfaces of the eye. With this, for example, a measurement can be done of the eye in a certain position and then, the measured shape of the eye can be compared with this reference position. Said device measuring shapes of surfaces of the eye can also be used for following constantly the movements of the eye, and from those the actual position of the eye can be calculated, if the starting point is known. If the device comprises two or more camera arrangements, the arrangement for recognizing the position of the eye can be realized by using for recognizing the position of the eye a camera arrangement that is at that point not actively imaging the eye. This can also be realized by studying the angle of back-reflections of the eye.

Said calculations of the position of the eye are preferably performed in the control arrangement or in a calculation or data processing arrangement connected to it. The arrangement for recognizing the position of the eye can naturally be a separate component that follows and, when necessary, makes calculations of the position or movements of the eye or eyes, or both, and transmits the information of these to the control arrangement.

The gaze guidance arrangement is designed for improving the examining of the eye in a way that the object from whom the observation is desired to be performed, helps the observing process by moving her/his eye or eyes guided by the equipment. Thus, for example, an arrangement designed for imaging of eyes can be realized where the cameras meant for the imaging do not need to move as much as they would need to move if the gaze was not guided. Further, it can be considered, that by means of the gaze guidance, either with a motor arrangement moving the cameras or without it, an imaging arrangement is achieved where the position of the eyes of the object to be imaged is made optimal, for example, from point of view of reflections or the certain object to be observed. A corresponding benefit can be considered to be achieved also in different measurements performed on the surface of the eye or in close proximity thereto. This kind of measurements can include, for example, measurements of concentrations of different substances in the human organism.

The gaze guidance arrangement guides the object to be imaged to look at certain directions such that, for example, the camera arrangement gets the next imaging area to be imaged. The gaze guidance arrangement can also be provided for guiding the eye to a position where no reflection takes place or it is minimized when the image analysing arrangement defects a reflection in the image taken or in the Image area before imaging. Correspondingly, the gaze guidance arrangement can be provided for guiding the gaze such that the same patient can be imaged every time at the same place or in the same position of the eye. Thereby, the guiding parameters of the gaze guidance arrangement are stored in a patient-based fife that is introduced when starting the imaging. The control arrangement can download this file, for example, from an external server. The gaze guidance arrangement provides a visual target, for example, on an internal LCD display of the device, where a dot, figure or area or similar is shown that the patient is supposed to took at. This visual target is moved according to how and to which position the eye is desired to move. The arrangement of presenting the visual target of the gaze guidance system can also be realized, for example, by a laser light, or reflecting the gaze guidance pattern directly onto the retina of the eye. The arrangement of presenting the visual target of the gaze guidance system can also be moved by a motor arrangement. Operation of the gaze guidance arrangement is controlled by the control system based on the imaging to be performed.

The gaze guidance arrangement can be, for example, inside a device designed for examining an eye or eyes when the device is operated by the person himself/herself, or in a desk-top device in a device designed for examining an eye or in a completely separate functional unit, for example, on a desk in a patient room. The gaze guidance can take place so that when the examining arrangement is such that it covers partly or completely the eye or eyes of the object to be examined, the gaze guidance is performed by an arrangement realized in front of the eyes of the person to be examined. Correspondingly, when the eyes are only partly or not at all covered, the gaze guidance can be considered to be realized so that the observing point meant for the gaze guidance or an area or a colour is presented on the surfaces of the room, for example, by reflecting the laser point to be observed onto the wall of the patient room or by displaying it, guided by the gaze guidance system, as patterns on the screen of a computer.

The main purpose of the gaze guidance can be considered to be facilitating, speeding up or improving the imaging of the eye fundus or surface of the person to be examined. By means of the gaze guidance, for example, a partly or completely reflection-free imaging arrangement can be realized in eye fundus imaging.

The gaze guidance arrangement is controlled through the measuring or imaging arrangement measuring or imaging the object. From the point of view of the imaging, it is the most optimal to perform the imaging with as small number of images as possible in relation to the performance of the device, and from the point of view of the measuring as quickly as possible and with good measurement results again in relation to the ability of the measurement arrangement to obtain measurable material of the eye or its surrounding.

The device performing the imaging can comprise a motor arrangement guiding the camera arrangement to the most appropriate position from the point of view of the imaging if the imaging can not be performed in the basic position of the camera arrangement. Further, in order to facilitate the operation of the motor arrangement and to speed up the imaging process, the device can be considered to comprise one or more gaze guidance systems that are introduced controlled by the control arrangement such that, for example, the motor arrangement moves the camera arrangement in front of the eye in one direction, and the person to be examined is guided to look elsewhere by the gaze guidance. Thus, the device designed for examining an eye is made small-sized and quick.

By the gaze guidance arrangement an embodiment can be realized, whereby the device does not comprise a motor arrangement designed for moving the camera arrangement, but the controlling of the imaging is realized merely by gaze guidance, i.e. the eye is guided to different positions in the imaging field and thus the imaging area is covered. Movements of the parts of the device and the gaze guidance can also be combined. Imaging can also be realized such that by the gaze guidance arrangement the gaze of the object to be imaged is guided to certain spots, and the camera arrangement takes an image or images, and the direction of the imaging of the camera arrangement is slightly adjusted.

Thus, the movements required by the camera arrangement can be reduced in comparison with a situation where the gaze direction of the object remains unmoved, and the equipment can be simplified.

The gaze guidance arrangement can be a separate, for example, standing on a table, for example, reflecting a laser light or lights onto the wall that is capable of operating independently without a connection to the device that performs the measuring or imaging of the eye, or its operation is such that showing of the reflections of the pattern on the wall is guided, for example, to avoid reflection areas detected by camera in front of the eyes of the person to be examined, the calculated next viewing angle in relation to the position of the cameras inside the device here in front of the eyes in relation to the surface or surfaces of the eye or eyes.

One alternative for realizing the gaze guidance arrangement in the case that the device where it is located, covers partly or completely the eye or eyes to be examined, is to show the image of the environment inside the device instead of showing the whole laser point or light area or a standard view in the internal display or similar. Thereby, the device in front of the eyes of the person to be examined comprises a camera or cameras that image the environment and which image will then be shown to the person being examined. This image may be provided further with separate gaze guidance spots.

FIG. 2 shows an example of bringing the eye into the desired position by the gaze guidance arrangement. A device (not shown in the Figure) is provided for examining the eye 201, the device comprising a camera arrangement 202 and a visual target 203 belonging to the gaze guidance arrangement. In FIG. 2a the viewing angle of the eye is directly towards the camera arrangements and the visual target. In FIG. 2b, the visual target has changed its place compared with FIG. 2a. The eye follows the visual target, and in FIG. 2c, the viewing direction is again directed to the visual target, and the camera sees the eye in a different position than in FIG. 2a.

FIG. 3 shows another example of bringing the eye into the desired position by the gaze guidance arrangement. A device (not shown in Figure) comprising a camera arrangement 302 is provided for examining the eye 301, and the eye is desired to be imaged at points A and B. In FIG. 3, the camera arrangement can take an image of point A. For the camera arrangement to be able to take an image of point B, it has to be moved inside the device to the point and position shown in FIG. 3b. FIG. 3c shows a visual target 303 belonging to the gaze guidance arrangement. This guides the eye to the position where the camera arrangement can take an image of the eye at point B and is substantially at the same position as in FIG. 3a. Thus, unnecessary moving of the camera can be avoided. The point at which the visual target is placed in order to bring the eye to the desired position is called the gaze guidance point, it is to be noticed that the desired position of the eye is not necessarily the position at which the viewing direction of the eye is towards the gaze guidance point, but the position can be reached already during the movement of the eye.

FIG. 4 shows an example of a gaze guidance arrangement according to the invention placed in the device 402 for imaging the eye 401. The device is broadly and as to its operating similar to what is described above. The device comprises a camera arrangement 404, the first illumination arrangement 403 and the second illumination arrangement 407. The device further comprises a gaze guidance arrangement that consists of arrangement of showing a visual target and control arrangement 408 that controls the arrangement of showing a visual target according to the stored instructions. Furthermore, the control arrangement controls other operation of the device, such as the camera arrangement and the illumination arrangement and data processing and possible communication with other devices, in addition thereto, in connection with the control arrangement there is an image analysing arrangement 408. The image analysing arrangement works as an arrangement for recognizing the position of the eye.

The camera arrangement 404 consists of optics a and a camera sensor b. The camera sensor can be formed of one or more light-sensitive parts. These photo-sensitive parts can detect for example visible light, IR or UV radiation or a restricted wavelength area. The camera sensors can be realized, for example, by a multi-spectral or hyperspectral technique. By a camera arrangement images or videos can be produced. A camera arrangement can be provided for monitoring by means of IR radiation reflection points of an eye and for storing them for use during the actual imaging.

The optics a can be fixed or arranged to be movable or detachable. The optics can be adjustable, i.e. it can be, for example, focused. This can be performed by a motor arrangement. These focusing and other adjustments can be realized also by moving the camera sensor or by moving the both; the camera cell and the optics. One part of the camera sensor can use several optics of different size or a combination thereof. Likewise, set of optics can be arranged to direct the light to several different sensors simultaneously. Further, in combination with the optics there may be dimmers or shutters or other similar parts. The optics can also be realized, for example, by liquid optics. It is essential that the optics is provided for directing the light in a desired way to the image sensor for performing the imaging. The optics may consist of several parts. The optics can also realize several functions in the device; it can, for example, realize the imaging and directing of the light to the eye.

In addition to moving individual parts, the camera arrangement can be movable also as a whole like in FIG. 3b. These can be realized by a motor arrangement. A possible motor arrangement is realized such that the motor arrangement guides the camera arrangement by possible axes x, y and z in relation to the surface and pupil of the eye. The motor arrangement can also be adapted to rotate or incline the camera arrangement.

The control arrangement is provided for controlling the pair of optics and camera sensor of the camera arrangement 401 and the first illumination arrangement 403 and the second illumination arrangement 407 automatically, according to its instructions. An illumination arrangement best suitable for each imaging case is selected. The control arrangement can perform the detecting of the object and focusing on it by the camera arrangement.

The arrangement 405 of showing the visual target can, for example, be a display that is located in the device such that it is in front of the eye 401 when the device 402 is in its place for imaging or other examination. The display can be, for example, a LCD display or a similar device. The arrangement of showing the visual target receives instructions from the control arrangement 408 and forms in the display a pattern that is distinguished from the surface. This pattern is a visual target to which the eye is supposed to be directed to such that the viewing direction and at the same time the position of it changes. The location of the visual target in the display is such that the position of the eye is the one desired or that the eye reaches the desired position while its viewing direction moves towards the visual target. In the display, single points, areas of the same or different colours or colour gradients or single patterns. There can, naturally, be several displays. Examples of visual targets formed in a display are disclosed in FIGS. 6 and 7.

Instructions about which points in the eye are to be imaged are stored in the control arrangement 406. Further, instructions about the fact whether when imaging the points in question the eye needs to be in a certain position, are stored in the control arrangement. If the eye 401 is meant to be in a certain position for an examination, for example, for said imaging, the control unit gives the instructions for the arrangement of showing the visual target 405 to show the visual target, whereby having the viewing direction directed to it the eye would be in the desired position. The control arrangement follows the position of the eye by means of the image analysing arrangement 408. The control arrangement can also follow other arrangements in order to recognize the position of the eye.

The control arrangement can have stored in it the path of the visual target in said display and the camera arrangement takes images when the eye is in the desired positions, i.e. when the arrangement for recognizing of the position of the eye recognizes that the eye is in the desired position. The control arrangement can also use the arrangement for showing the visual target 405 to guide the position of the eye to a slightly different position, for example, if a reflection or other factor inconveniencing the examination was detected in the image or image area. Thereby, the control arrangement instructs the arrangement for showing the visual target to form a visual target, the location of which being such that the viewing direction and the position of the eye change slightly in relation to said previous position of the eye where a drawback was defected. The predetermined position of the eye can thus be stored in the memory of the control arrangement prior to the examination performed with device 402, or the control arrangement forms said position when necessary. The control arrangement can, for example, have as instruction for changing the position of the eye during the imaging to find a new position for imaging the eye, whereby the viewing direction deviates by a determined number of degrees from the original viewing point, where the disadvantage was detected. This disadvantage can be, for example, a reflection in the image area, and this reflection can be removable by changing the direction of imaging.

The arrangement for showing a visual target 405 can, in addition to a display, be also, for example, a group of stationary light sources, such as LED lights that are switched on and off according to the instructions from the control arrangement. The arrangement of showing a visual target can also be one or more stationary light sources, the illumination direction of which is changed in relation to the eye. Adjusting of the illumination direction can be realized by changing the position of the light source or by placing optics between the eye and the light source, by which optics the direction of the light or focusing or both can be adjusted. The light source or sources can also be movable inside the device such that the location of the visual target produced by them in respect of the eye can be changed. Also a laser source can serve as light source. By this a visual target can be formed by illuminating directly to the surface of the eye, to the inner parts of the eye in different depths, or to the fundus of the eye. These direct illuminations towards the eye can also be realised such that the direct illumination is performed through the optics of the camera arrangement or that the direct illumination is performed from the side of the camera sensor of the camera arrangement or through the camera sensor. The direct illumination can also be realized in connection with the image pixels of the camera sensor so that part of the pixels or of the area between the pixels works as the light source.

The aim is to form the visual target in a way that it is sharply visible to the object of the imaging. The visual target can be changed according to the Information of the dioptre of the eye. This information can be obtained in advance, or the system detects the dioptre of the eye and forms the visual target accordingly. This focusing of the visual target can be performed, for example, as follows. If the arrangement includes optics, ultrasound, laser or a similar arrangement that is directed and focused into the fundus of the eye and measures this distance, this distance is utilized in order to show sharply the visual target at a desired distance. Also a pattern can be reflected to the fundus of the eye, and the device comprises an optical arrangement, the focusing of which can be changed to be similar to the actual eyesight of the person to be imaged is. In general, a visual target at a certain physical distance from the surface of the eye can be shown so that it is sharp to most of the persons whose eyesight is normal. This visual target can be shown in different definitions and the one can be chosen that the person to be imaged seems to have the best response to in different directions of the view of the eye, which can, for example, be the fact that the eyes are not blinking or wandering. Thereby, the focusing in question is the focusing value that is given for each visual target during the imaging.

The forming of the visual target in the device can be performed also by indirect illumination. Hereby, to a surface inside of the device a pattern is illuminated that forms the visual target of the gaze guidance arrangement. The surface can be reflective, it can also be made of milk glass or similar material. Onto this surface by means of a light source a visual pattern, for example, a dot is reflected that spreads on a diffuse surface. Thereby, the viewing direction of the object can be directed to a certain area, for example, by means of a colour instead of that the object would need to look accurately at a certain light. This opalescence material can also be used in connection with direct illumination. The indirect illumination can also be performed, for example, to a reflective surface or subarea inside the imaging optics. The surface of the indirect illumination can be behind, next to or in front of the camera or measuring arrangement. The surface can be semi-transparent, i.e. partly translucent, whereby the camera arrangement can image through it. There can, of course, be several surfaces of indirect illumination, and they can be movable. A semi-transparent surface can also be such that the visual target can be reflected onto it from different angles, whereby the visual target seems to be at a different distance for the viewer than the surface in question thanks to the optical structure in front of the system. This partly translucent surface can be formed so that a dot or image reflected onto it from the side seems whole and being in perspective to the viewer.

The visual target can also be formed by an illumination arrangement of the device. The illumination arrangement can be such that it is thereby not actively used for examining an eye or it is used to guide the eye to the desired position, and when the eye is in the position in question, it is used to illuminate the eye for imaging.

There can be several arrangements of showing a visual target of different types in the device, and they can be used alternately or, when necessary, simultaneously.

The arrangement of showing a visual target can be performed such that it is common for both eyes or there is an individual arrangement for both eyes, respectively. The visual target can be shown to the eye dedicated to it, for example, by optical guidance, or the arrangement of showing a visual target is movable inside the device to be at the place of the eye to be guided. This can also be realized so that in the device an arrangement of showing a visual target is common for both eyes, and some are meant for one eye.

In a device, comprising the same internal arrangement of showing a visual target for both eyes, the visual target may be a target observed through a common optical structure, such as a prism arrangement, for both eyes. This may be a target in the display, a light source, a laser source or a reflection area. The visual target is produced for both eyes substantially at the same point, i.e. both eyes have the same gaze guidance point. Thereby it can be confirmed that both eyes are moving. The structure can be optically such that the visual target is sharply visible from all viewing distances and angles for both eyes. The optical structure can be optics in front of both eyes that is directed at the visual target to be viewed. It can also be a so called waveguide structure that guides the Sight, shape or display to the front of the eye at a desired distance from the surface of the eye and with a sense of the desired distance to the front of the eyes. Although the arrangement of showing a visible target would be the same for both eyes, when necessary, it can be used only in front of one eye, if for example the camera arrangement covers the other eye completely. The optical structures described here can of course be applied in the device where there is an individual arrangement of showing a visual target for both eyes, respectively.

If there is a separate system of showing a visual target for both eyes, they can be switched separately for both eyes or they can be used simultaneously. An individual system of showing a visual target for both eyes enables auto stereoscopic gaze guiding. Since the system of showing a visual target is separate for both eyes, gaze guidance can be performed so that for both eyes a different visual target is shown in the same point or gaze guidance point in the same shape, or in a different point and in a different shape or colour if, for example, illumination of a newly taken image causes that the look can't be directed correctly for a while.

The internal system of showing a visual target can be realized by showing an external image to the object being examined. Thereby, for example, in the front part of the device, i.e. in the part opposite to the eyes, there is a camera that images an external view. This image is shown inside the device. The image can be prepared to include further the own gaze guidance point or colour or shape produced by the device. The control arrangement of the device can be instructed also to detect a target in the view, for example, a laser point pointed by the user of the device, as the visual target.

The gaze guidance arrangement can be passive or active. The passive gaze guidance arrangement does not necessarily change the given visual target. The arrangement guides the gaze to certain predetermined points in relation to the previous point. If the measuring, observing or imaging performed by the device is successful, the gaze is guided by the gaze guidance arrangement to a new point. If the measuring, observing or imaging is unsuccessful, the gaze is guided to another point. This point can be, for example, between the previous and unsuccessful point, for example, in the middle. The point can also be completely new. In general, the space between the gaze guidance point shown in the gaze guidance arrangement and the gaze guidance point shown next is a certain measurement or angle. The gaze guidance point is changed according to the programming, and if there is not a changed result of measurement, imaging or observing for successive points during the imaging, the gaze guidance point is brightened or its showing starts from beginning. That is, in passive imaging, the viewing direction is guided by a movement of a visual target from the gaze guidance point A to the point B, and the measuring, observing or imaging is performed not until the gaze is found to be directed to the direction shown by the gaze guidance point B. Here, points A and B signify the points stored in the control arrangement, at which the gaze is meant to be directed in the arrangement. A passive gaze guidance method can also be performed such that the motorized camera system possibly existing in the device moves to the calculated optimal angle in regard to its shown gaze guidance point at the moment, if the image can not be taken either due to reflection in the imaging area or because the target in the eye is not visible at ail or properly because the gaze was obviously not turned according to the instructions, the apparatus gives a new gaze guidance point. After this, the camera moves again in regard to the calculated optimal angle from this given gaze guidance point.

In an active gaze guidance arrangement, in addition to the position of an eye also other quantities are observed. Hereby, for example, quantities related to the viewing direction, such as speed, direction, uniformity and limits, or shapes and reflectivity or change of the size of the pupil or its velocity, can be observed. Furthermore, movements of the head, such as speed, direction, uniformity, limits and relations to movements of the eye, can be observed. The movements of the head can be observed, for example, by an accelerator or similar arrangement installed in the device. By the measured other quantities the operation of the gaze guidance arrangement is controlled or they can be stored and, for example, be attached to the images or to be sent to an external device for additional analysis or storage. The active gaze guidance arrangement can, for example, change the visual target due to wandering of the guided eye, for example, by increasing and reducing the size of the visual target or by changing the colour or shapes of the visual target between different gaze guidance points, for example, because the object being imaged does not see exactly the certain colour or pattern well enough.

The active gaze guidance arrangement produces, when necessary, another gaze guidance point. Thereby, the gaze guidance point is changed dynamically during the whole need of the gaze guidance. The place can be optimized, for example, for the part of the most optimal observation. Thereby the user of the device can perform optical observation, for example, through the device. The place can be optimized also, for example, for the part of the most optimal view angle for the imaging of the surface of the eye or fundus of the eye performed by the camera arrangements. Optimizing can be used for removing reflection or similar imaging artefacts or reducing them in images or image area. That is, in the active glaze guidance observation is performed also in area between the gaze guidance points A and B. Thereby, a dynamic observation can be done from the point of view of the most optimal measurement, observation or imaging. The device can make an action even if the gaze would not be guided to the direction determined by point B.

In the active gaze guidance arrangement the ability of the object to notice the next given visual target can be observed. Hereby, for example, the speed of the eyes to change from the gaze guidance point A to point B or wandering of an eye or eyes, for example, due to tiredness between gaze guidance points A and B can be observed. Furthermore, for example, possible alternating of the active eye in observing of the gaze guidance point caused by errors of refraction of the eyes can be observed which causes, for example, reciprocating motion in the eyes. Furthermore, for example, the movement of the head of the object can be observed in relation to motions of the eyes. Thereby, the gaze guidance arrangement can control the visual target at the same time.

When necessary, the active gaze guidance arrangement also switches off the gaze guidance, if the evaluation about the tracking ability of the gaze guidance towers or the tracking fails completely. For example, there are too many successive points or areas to be tracked, too much of the same colour in the gaze guidance points, or if an illumination arrangement makes the observing ability of a colour or shape to lower temporarily, the eye does not observe the new point. The gaze guidance can be switched on to wait that the apparatus recognizes that the gaze is directed to the angle where the gaze guidance point is located.

In general, the device with the gaze guidance arrangement is provided to switch on the gaze guidance arrangement, when necessary, or by programming. As the device is placed to the front of the eyes, it may happen that the eyes of the person being examined either look directly forward or start directing onto the centre axis, whereby the viewing direction of the eyes is crossed. This is why the control arrangement of the device, when necessary, detects the viewing direction prior to the Imaging and switches on the gaze guidance, so that, for example, the possible fixed cameras are able to perform the imaging. Naturally, if the device is optically capable enough, the gaze guidance can be left not switched on, even if the most optimal camera angle in relation to the eyes is not achieved, if the view is, however, large enough or, for example, without reflections. Thus, this means, for example, a situation where the device is such that it is placed to the front of the eyes or held in the front of the eyes, and inside the device there is an optical arrangement for both eyes that can take an image of the fundus of the eye with a large camera angle. Even if the apparatus would be equipped with motors moving the camera arrangement and with a gaze guidance arrangement, neither one needs necessarily to be switched on, even if the viewing direction of the object being imaged is not such that the imaging area of the fundus of the eye would be the most optimal. If the system detects, that the image will be achieved from an area large enough, the imaging switches on without the gaze guidance and motors moving the camera arrangement.

Figure 5:
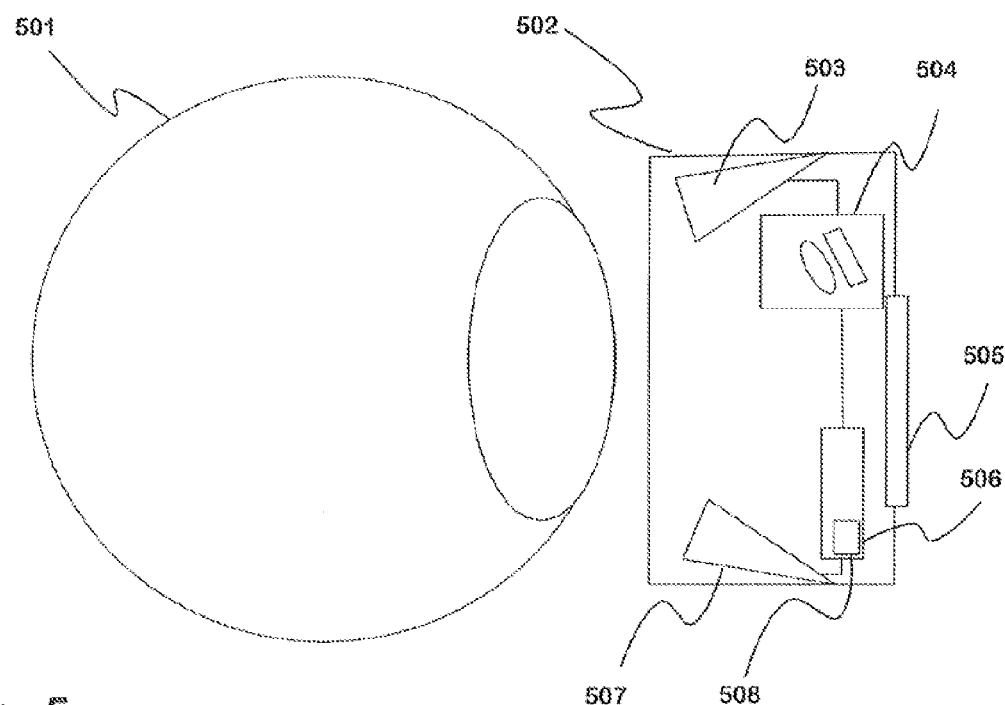
FIG. 5 shows another example of a gaze guidance arrangement according to the invention located in a device.

FIG. 5 shows an example of a gaze guidance arrangement according to the invention placed in the device 502 for imaging the eye 501. The device is broadly and as to its operation similar to what is described in the example of FIG. 4. The device comprises a camera arrangement 504, the first illumination arrangement 503 and the second illumination arrangement 507. The device further comprises a gaze guidance arrangement that consists of an arrangement of showing a visual target and a control arrangement 506 that controls the arrangement of showing a visual target according to the stored instructions. Furthermore, the control arrangement controls other operation of the device, such as the camera arrangement and the illumination arrangement and data processing and possible communication with other devices. In addition thereto, in connection with the control arrangement there is an image analysing arrangement 508. The image analysing arrangement works as an arrangement for recognizing the position of the eye. Distinguished from the example of FIG. 4, the arrangement of showing the visual target of the device 502 is outside the device, in order for the object being imaged to see the visual target when the device is in operating position in front of the eyes, the device comprises at least a partly light transmitting surface 505 through which the gaze can be directed. The arrangement of showing a visual target can be, for example, a pattern shown in a display or reflected onto the opposite wall that is visible through the surface in question. By movements of this pattern the gaze direction of the eye is guided correspondingly to what was described earlier. This tight transmitting surface can be protected by a plate or similar that is moved away from the surface when the gaze guidance is required.

The arrangement of showing a visual target of the device 502 can be, for example, a display, a monitor or a pattern reflected by the device. It can also be an arrangement with several static objects of which one is chosen alternately to be the visual target. This choice can be automatic, for example, lights are switched on as visual targets, or it can be performed manually, whereby, for example, the user of the device points with a laser light at a target. The arrangement of showing a visual target or the device controlling it can have a connection to the control arrangement 508 of the device 502 for transmitting information about the location of the visual target. The device 502 can comprise an arrangement that recognizes in which direction the visual target is in comparison with the device, and this arrangement transmits the information to the control arrangement. This arrangement can be, for example, a camera. The arrangement can also recognize if, for example, a visual target reflected onto a wall does not stand out from a wall, for example, due to ambient light or material of the wall. The control arrangement 506 can also transmit instructions to the arrangement of showing the visual target or to the device controlling if in order to move the visual target.

Figure 8:
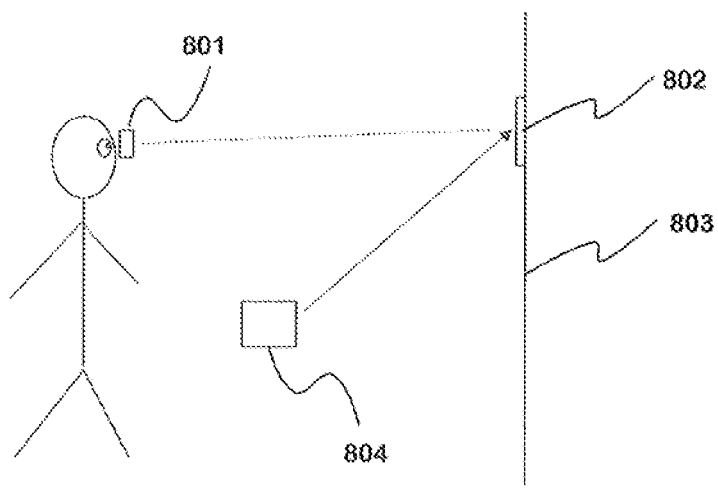
FIG. 8 shows a third example of the device and the gaze guidance arrangement according to the invention.

FIG. 8 shows an example of the device 801 with an external arrangement of showing a visual target. The visual target 802 is in this example formed by a laser device 804 onto a surface 803 that can be a wall. The laser device is in this case close to the object being examined, for example, on a desk. The device forming the visual target can also be located in the device for examining the eyes. The object being examined can direct her/his gaze through or by the device 801 to the visual target. The control arrangement can observe the movement of the head of the object in relation to the movements of the eyes. Thereby, the visual target can be moved simultaneously, for example, in relation to the movements of the head either in the same direction or in an opposite direction. By observing the movement and position of the head it can be recognized when the object being examined is looking, for example, by the display, and thereby, the object to be examined can be instructed to look at the right direction, for example, by a voice message or sound signal or a light or similar.

It is to be noticed that the device can comprise simultaneously both an internal and an external arrangement of showing a visual target. Besides, the device can comprise several different types of arrangements of showing a visual target.

Figure 6:
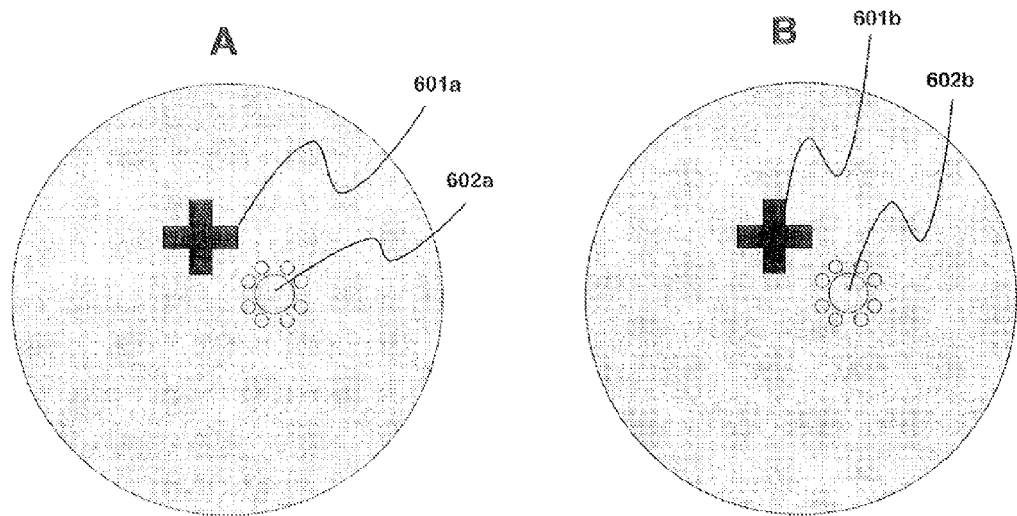
FIG. 6 shows an example of a visual target of a gaze guidance arrangement according to the invention.
Figure 7:
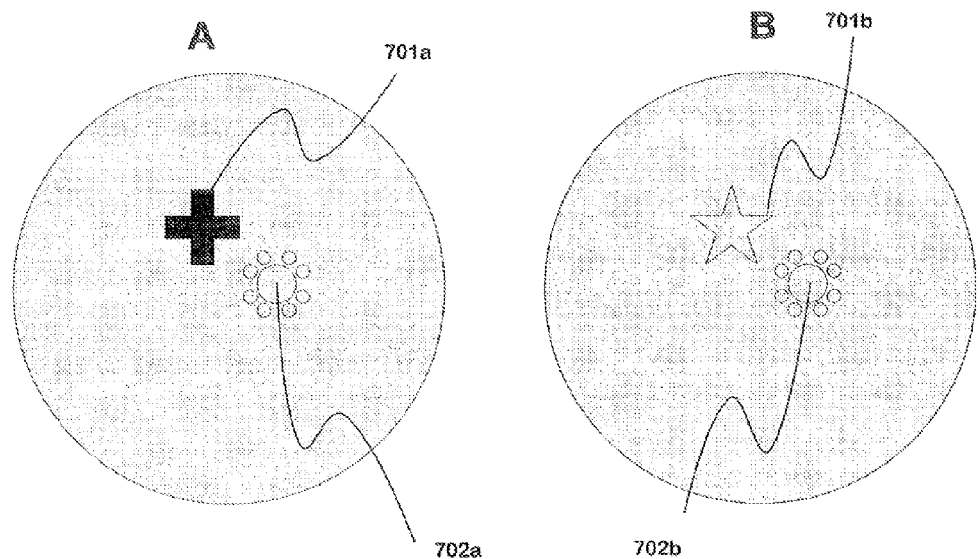
FIG. 7 shows an example of the operation of a gaze guidance arrangement according to the invention, when it is outside the device.

In FIGS. 6 and 7, examples are shown of showing a visual target to the object being examined. In the Figures, point A shows a view produced for eye A and point B shows a view produced for eye B.

FIG. 6 comprises an arrangement where the same visual target 801 is shown for eye A and eye B. The arrangement comprises the first camera arrangement 602a that images the eye A, and the second camera arrangement 602b that images the eye B. The camera arrangements are surrounded by a group of illumination arrangements. This arrangement comprises one internal arrangement of showing a visual target, and by it is produced the visual target 601a for the eye A and the visual target 601b for the eye B. The visual target is divided by an optical arrangement for both eyes such that the view is equally sharp for both eyes. In focusing, errors of refraction or other dissimilarities of the eyes can be taken into consideration. Also an individual visual target can be produced for both eyes, respectively, and those are synchronized. When moving the visual target, the gazes of the eyes follow it and settle to a position. When the position of the eye or eyes is the one desired, the camera arrangement takes an image of the eye or the camera arrangements take an image of both eyes, respectively. By the arrangement according to FIG. 6, the eyes are made move in the same step.

FIG. 7 comprises an arrangement where a different visual target 701 is shown for eye A and eye 8. The arrangement comprises the first camera arrangement 702a that images the eye A, and the second camera arrangement 702b that images the eye B. Here, for both eyes there is an arrangement of showing a visual target. For eye A, a visual target 701a is produced and for eye B, a visual target 701b is produced that differ from each other, for example, by shape, colour, brightness, and polarisation or by other features or combinations thereof. The visual targets can be produced alternately or at the same time whereby stereoscopic or polarized patterns can be provided.

Several visual targets can be shown simultaneously. The arrangement follows the gaze, and the visual targets to which the gaze is not directed, can be switched off or dimmed. Switching off can be performed in a way that all other visual targets but the one to be viewed are switched off or the visual targets near the visual target to be viewed are left switched on but dimmer. The visual targets can be of different definitions, or their definition can alternate before the gaze is directed. The definition of a visual target can alternate also after the gaze is focused at a target or area with several targets. Visual targets shown simultaneously can move either all in one group or individually and, for example, so that some of them move and some not.

The arrangement can be performed so that the gaze guidance arrangement can be switched off, if there are problems in guiding the gaze, for example, due to wandering of an eye or blinking of an eyelid.

Above, some preferred embodiments according to the invention have been described. The invention is not limited to the solutions described above, but the inventive idea can be applied in numerous ways within the scope of the claims.

The invention claimed is:

1. A gaze guidance arrangement provided to guide the movement or position of the eye or both, the gaze guidance arrangement comprising: a visual target, to which the eye is meant to be directed, wherein said gaze guidance arrangement further comprises a control arrangement that is provided for controlling the gaze guidance arrangement, the control arrangement being at least partly located in a device being provided for examining an eye or eyes to be placed on the head of the object or to the front of the head of the object, the device further comprising one or more camera arrangements and one or more illumination arrangements, and the optical axes of the camera arrangement and the illumination arrangement used in the same imaging are in different directions or substantially apart from each other in relation to the eye, and said control arrangement is further provided to guide said camera arrangement and illumination arrangement, and the control arrangement is provided to switch the camera arrangement to take automatically one or more images of the eye when the eye is in a predetermined position to which the visual target of said gaze guidance arrangement has guided said eye when the device is ready for operation in front of the eye, and one or more target formation arrangements that is provided to form said visual target the location of which in respect of the eye or the direction of view of the eye or to both can be changed, and the location of the visual target is determined such that as the eye is directed to the visual target or in a direction of the visual target, it is in said predetermined position, wherein further the gaze guidance arrangement comprises an image analysing arrangement which, after detecting light of the illumination arrangement reflected from a surface of the eye detected in the taken image or in an image area before imaging, provides the gaze guidance arrangement to guide the eye to a position where no reflection takes place or the reflection is minimized.

2. The gaze guidance arrangement according to claim 1, further comprising an arrangement for recognizing the position of the eye, and the control arrangement is provided to switch the camera arrangement to take automatically one or more images of the eye, when the arrangement for recognizing the position of the eye has recognized that the eye is in a predetermined position, to which the eye was guided by the visual target of said gaze guidance arrangement.

3. The gaze guidance arrangement according to claim 1, wherein the control arrangement is provided to guide the location of the visual target formed by the target forming arrangement according to the predetermined position of the eye.

4. The gaze guidance arrangement according to claim 1, wherein said device comprises a sensor arrangement for detecting the movement or the position of the device or both, and said sensor arrangement is provided to transmit the detected information to the control arrangement that is provided, according to predetermined instructions, to change the operation of the gaze guidance arrangement by changing the location of the visual target according to the information of said sensor arrangement.

5. The gaze guidance arrangement according to claim 1, wherein the gaze guidance arrangement is located partly outside of said device, and the device is provided so that when the device is in its place and ready for operation, the viewing direction of the eye to be guided is through the device or passing by the device, and the part outside of the device is at least a part of the target forming arrangement.

6. The gaze guidance arrangement according to claim 5, wherein the target forming arrangement outside of the device is a display on which it is possible to form said visual target, or that the target forming arrangement is a surface, on which said visual target can be reflected by a light source arrangement capable of being controlled.

7. The gaze guidance arrangement according to claim 5, wherein a recognizing arrangement associated with said device that recognizes the location of the visual target, the location being provided to be transmitted to the control arrangement.

8. The gaze guidance arrangement according to claim 5, wherein the visual target is at least during the guidance of the eye immobile in order to achieve at least one predetermined position of the eye, and in operation mode the immobile device is arranged to be movable.

9. The gaze guidance arrangement according to claim 5, wherein the visual target is provided to be movable according to the movements of the device such that the location of the visual target in respect of the direction of the viewing of the eye remains substantially the same.

10. The gaze guidance arrangement according to claim 1, wherein at least one target forming arrangement is located in said device.

11. The gaze guidance arrangement according to claim 10, wherein at least part of the target forming arrangement in the device is separate for both eyes, respectively, or that said at least part of the target forming arrangement is common for both eyes, and the device comprises an arrangement for moving said at least part of the target forming arrangement inside the device to the vicinity of the eye, the position of which is to be guided by the gaze guidance arrangement.

12. The gaze guidance arrangement according to claim 10, wherein the target forming arrangement in the device comprises an internal light source arrangement that is provided to form a visual target, the light source arrangement comprising one or more light sources.

13. The gaze guidance arrangement according to claim 12, wherein the internal light source arrangement of the device is provided to form a visual target by illuminating towards the eye.

14. The gaze guidance arrangement according to claim 13, wherein the internal light source arrangement of the device consists at least partly of the illumination arrangements of the device.

15. The gaze guidance arrangement according to claim 12, wherein the internal light source arrangement of the device is provided to form a visual target by illuminating a surface inside the device.

16. The gaze guidance arrangement according to claim 12, wherein when the device is standing still in operation mode, between the internal light source arrangement of the device and the eye guided by the gaze guidance arrangement there is an optics arrangement that may consist of one or more optical components, the optics arrangement being provided to form an image of the visual target at different distances in respect of the eye.

17. The gaze guidance arrangement according to claim 12, wherein at least one internal light source arrangement of the device comprises one or more light sources that are provided to be switched on and off according to the instructions of the control arrangement in order to form a visual target.

18. The gaze guidance arrangement according to claim 12, wherein at least one internal light source arrangement of the device comprises one or more light sources that are movable inside the device or the direction of illumination of which can be changed, or both, in respect of the eye guided by the gaze guidance arrangement.

19. The gaze guidance arrangement according to claim 1, further comprising an image analysing arrangement associated with said device, the image analysing arrangement being provided to recognize predetermined features or properties in an image taken by the camera arrangement or in the image area of the camera arrangement and to transmit the information to the control arrangement being provided according to predetermined instructions stored in the control arrangement and information of the image analysing arrangement to form a visual target, if the predetermined instructions become filled.

20. The gaze guidance arrangement according to claim 19, wherein the predetermined instructions stored in the control arrangement include at least one of the following: a reflection detected in the image or image area, success of imaging of a certain image area, failure of imaging of a certain image area, eye position or getting the eye to be in a certain position in respect on the camera arrangement.

21. The gaze guidance arrangement according to claim 1, wherein the visual target is dot-like or a pattern or a point deviant of its environment by its colour, the visual target being immobile or movable in order to provide the predetermined position or movement of an eye in respect of the camera arrangement.

* * * * *